(12) United States Patent
Tomita (10) Patent No.: US 6,824,660 B2
(45) Date of Patent: Nov. 30, 2004

(54) MOLECULAR RECOGNITION TYPE CHEMICAL CCD

(75) Inventor: Katsuhiko Tomita, Kyoto (JP)

(73) Assignee: Horiba, Ltd., Kyoto (JP)

( * ) Notice: Subject to any disclaimer, the term of this patent is extended or adjusted under 35 U.S.C. 154(b) by 279 days.

(21) Appl. No.: 09/750,357

(22) Filed: Dec. 29, 2000

(65) Prior Publication Data

US 2001/0017265 A1 Aug. 30, 2001

(30) Foreign Application Priority Data

Feb. 29, 2000 (JP) .................................... P. 2000-053678

(51) Int. Cl.[7] .............................................. G01N 27/26
(52) U.S. Cl. ........................... 204/416; 435/291; 435/6; 324/457; 257/253
(58) Field of Search ........................ 204/416; 435/291, 435/6; 324/457; 257/253

(56) References Cited

U.S. PATENT DOCUMENTS

| | | | | |
|---|---|---|---|---|
| 5,164,319 A | * | 11/1992 | Hafeman et al. | ......... 435/287.1 |
| 5,587,273 A | * | 12/1996 | Yan et al. | .................... 430/269 |
| 6,197,503 B1 | * | 3/2001 | Vo-Dinh et al. | ............... 435/6 |
| 6,203,758 B1 | * | 3/2001 | Marks et al. | .......... 204/403.01 |

FOREIGN PATENT DOCUMENTS

| | | | |
|---|---|---|---|
| DE | 43 38 732 A1 | 5/1995 | ......... G01N/27/327 |
| EP | 0 881 486 A2 | 12/1998 | ......... G01N/27/414 |
| JP | 9-236560 | 9/1997 | .......... G01N/27/00 |
| JP | 10-332423 | 12/1998 | ............ G01D/5/12 |
| JP | 11-201775 | 7/1999 | ............ G01D/5/18 |
| WO | WO 87/07033 | 11/1987 | ............. G01T/1/00 |
| WO | WO 96/27025 | 9/1996 | ............. C12Q/1/68 |

OTHER PUBLICATIONS

Eva Hedborg, et al.; "Some studies of molecularly–imprinted polymer membranes in combination with field–effect devices" 1993; pp. 796–799.

* cited by examiner

Primary Examiner—Mark L. Bell
Assistant Examiner—Jennine M. Brown
(74) Attorney, Agent, or Firm—Sughrue Mion, PLLC (57) ABSTRACT

A molecular recognition layer 21 is formed on a sensor face 6a of a chemical CCD 1 having such a structure that a plurality of potential wells 6 constituted to change a depth corresponding to a chemical quantity are arranged two-dimensionally, electric charges are injected into the potential wells 6, and the chemical quantity is converted into an electric charge corresponding to the sizes of the potential wells. Thus, it is provided a novel and useful molecular recognition type chemical CCD capable of measuring an ultramicro chemical substance with an ultrahigh sensitivity at a molecular level.

4 Claims, 8 Drawing Sheets

MOLECULAR RECOGNITION TYPE CHEMICAL CCD

BACKGROUND OF THE INVENTION

The present invention relates to a molecular recognition type chemical charge coupled device (CCD) capable of measuring an ultramicro chemical substance with an ultrahigh sensitivity at a molecular level.

In recent years, it has been required that an environmental pollutant such as dioxin or environmental hormone and protein such as a DNA are measured at a ppb (parts per billion) or ppt (parts per tera) level. The environmental pollutant such as dioxin or environmental hormone should be measured by ultrahigh sensitivity analysis because an ultramicro substance is to be measured.

As a method of measuring ultramicro dioxin or environmental hormone, an SAW (surface acoustic wave) device method and a surface plasmon method have been studied. In the former method, an object to be measured is caused to come in contact with a surface elastic wave device and is measured based on a shift of a resonance frequency, which has a very high universality. It is apparent that analysis of 1 ng (nanogram), that is, in order of 1 ppb can be carried out with a frequency shift of 0.1 Hz. The latter method utilizes light transmission from the inside of an optical material to the outside. In any of the methods, the measurement can be carried out with a high sensitivity. However, an expensive device such as an electronic circuit or an optical system is required over the whole measuring system for operating the device.

For example, DNA measurement has been carried out in the following manner. More specifically, sections of approximately 10 mm square are formed on the surface of a slide glass. Hundreds to hundred thousands of fixed regions having a size of 10 $\mu m^2$ including different probe DNAs from each other are arranged two-dimensionally in one section. One section acts as a DNA chip and has a size of 10 $cm^2$. A chip surface is immersed in and washed with a solution containing a target DNA previously subjected to a labeling treatment with a fluorescent material, and the target DNA complementary to the probe DNA is hybridized (associated) to remain on a surface. The hybridized DNA chip surface can be measured as a fluorescent image through a fluorescent laser microscope and a CCD camera, and automatic control is carried out by a computer to perform a data processing. There has also been software in which genes to correspond to positions of a light emitting spot are previously registered in the computer, a fluorescent material for emitting green and red lights having a resolution of 1 to 10 $\mu m$ is used to detect a feeble fluorescent intensity when forming a labeling piece, and hybridization profiles such as green and red signals or a yellow signal for double light emission can be compared in the same DNA chip.

However, the conventional method of measuring a DNA is based on a fluorescence method. The DNA to be measured is not directly measured. Therefore, there is a problem in that measuring precision basically depends on a conversion ratio. In addition, an expensive large-scale optical system is used. Therefore, there is a problem in that the whole device is expensive and large-sized.

In order to selectively and easily measure the object, a method of detecting a change in an electric potential of a functional substance as an ion selective electrode is the most effective. Examples of a method of directly and selectively measuring the substance to be measured include a mold polymerizing method (a molecular imprinting method). This method is also referred to as the mold polymerizing method in which a polymeric resin (host) and a substance to be measured (guest) are complexed and polymerized, and the guest is then removed to form a mold having a cavity in a portion of the host where the guest was present, and only molecules corresponding to the mold are taken out.

Examples of a method obtained by developing the mold polymerizing method include an interface mold polymerizing method. In the interface mold polymerizing method, a mold is formed on an oily water interface of a heterogeneous system in which a water layer and an oil layer are present together. The reaction to guest molecules does not reach the inside and is restricted to an interface. Therefore, there is an advantage that mass transfer is rapidly carried out and a response speed is higher than that of the ordinary mold polymerizing method.

In an electrochemical method, a change in a contact with environment pollution molecules can be directly taken as a signal. A large number of methods have been developed as a semiconductor sensor. In order to monitor an environmental polluting molecular concentration and to carry out remote sensing, the development of a gene manipulation technique of a microorganism and a useful function material is insufficient. For example, the remote sensing premises the field installation of an electronic device and plural sensing operations are required for real-time measurement.

There is a higher possibility that two-dimensional sensing might consequently obtain a new knowledge than the acquisition of an ultrahigh sensitivity of one sensor. According to simple calculation, it is possible to obtain a two-dimensional image signal including positional information in which face arrangement sensors of 4096, 16384 and 65536 correspond to a sensor in the two-dimensional sensing of 64×64, 128×128, and 256×256.

Furthermore, a technique for measuring bioimaging of molecules and cells has recently been developed remarkably. It is supposed that a device (chemical CCD) for transferring, through a CCD, electrochemical double layer surface charges generated on an interface between the environmental pollutant and the sensor will enable real-time two-dimensional chemical image measurement in the future. For the chemical CCD, it is proposed "Method and Apparatus for Measuring Physical Phenomenon or Chemical Phenomenon" in Japanese Patent Application No. Hei 9-157716 filed dated on May 29, 1997. The same has published as JP-A-10-332423 or EP-A-0881486. The structure and operation principle of the chemical CCD according to the patent application will be described below with reference to FIGS. 7 to 9.

Figure 7:
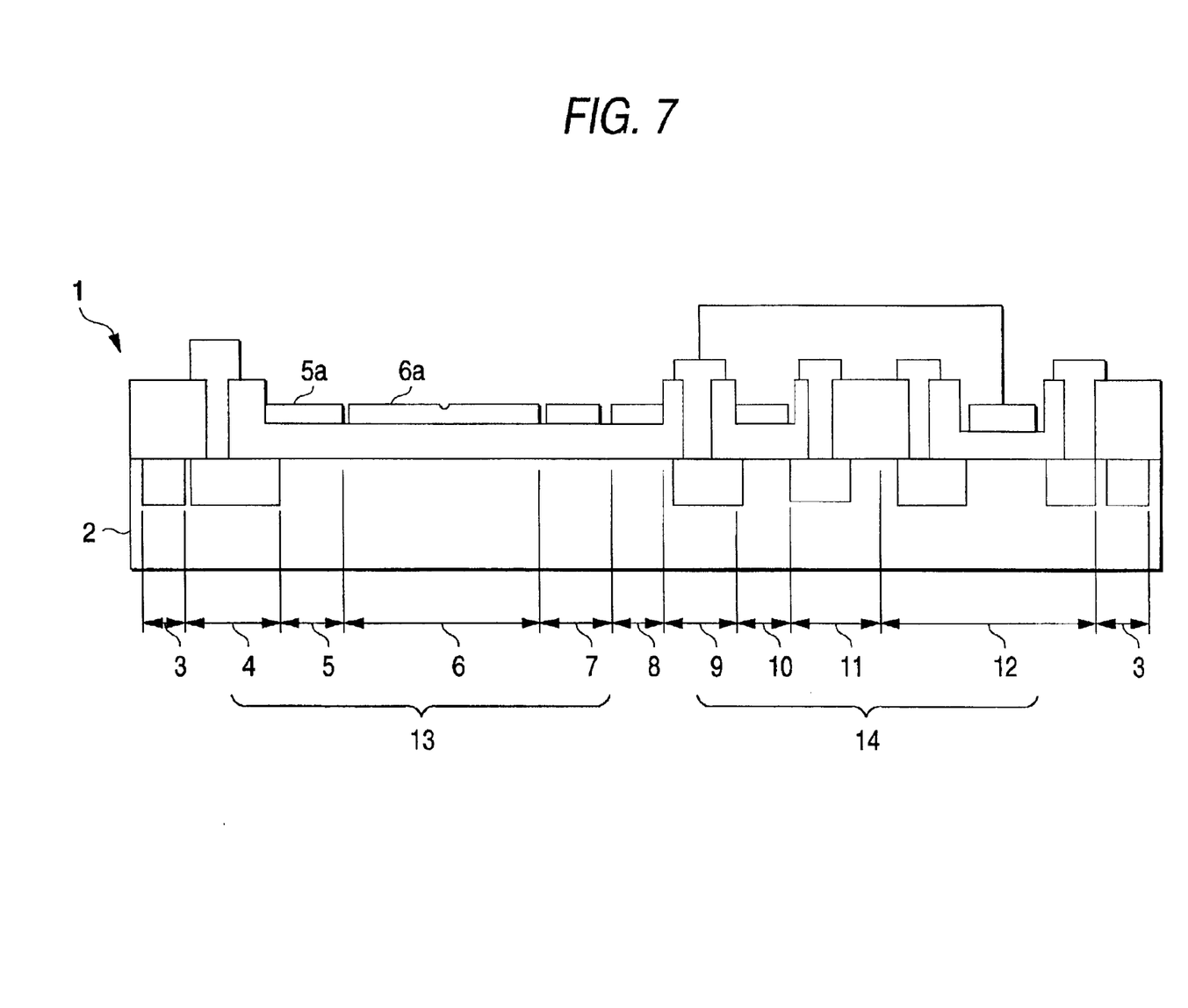
FIG. 7 is a view schematically showing the structure of a chemical CCD to be used for the invention.

In FIG. 7, the reference numeral 1 denotes a chemical CCD having the following structure. More specifically, the reference numeral 2 denotes a semiconductor substrate comprising p-type Si (silicon), for example, and has a thickness of approximately 500 $\mu m$. The semiconductor substrate 2 is provided with a channel stopper 3, a charge supply section 4, a charge injection adjusting section 5, a sensing section 6 to be a charge converting section, a barrier section 7, a charge transfer section 8, a floating diffusion 9, a reset gate 10, a reset drain 11, and an output transistor 12 having an MOS structure.

A sensor section 13 is formed by each of the charge supply section 4, the charge injection adjusting section 5, the sensing section 6 and the barrier section 7. The sensing section 6 is formed of a potential well constituted to change a depth corresponding to a chemical quantity, which will be described below in detail. Moreover, an output section 14 is formed by each of the floating diffusion 9, the reset gate 10, the reset drain 11 and the output transistor 12.

Figure 8:
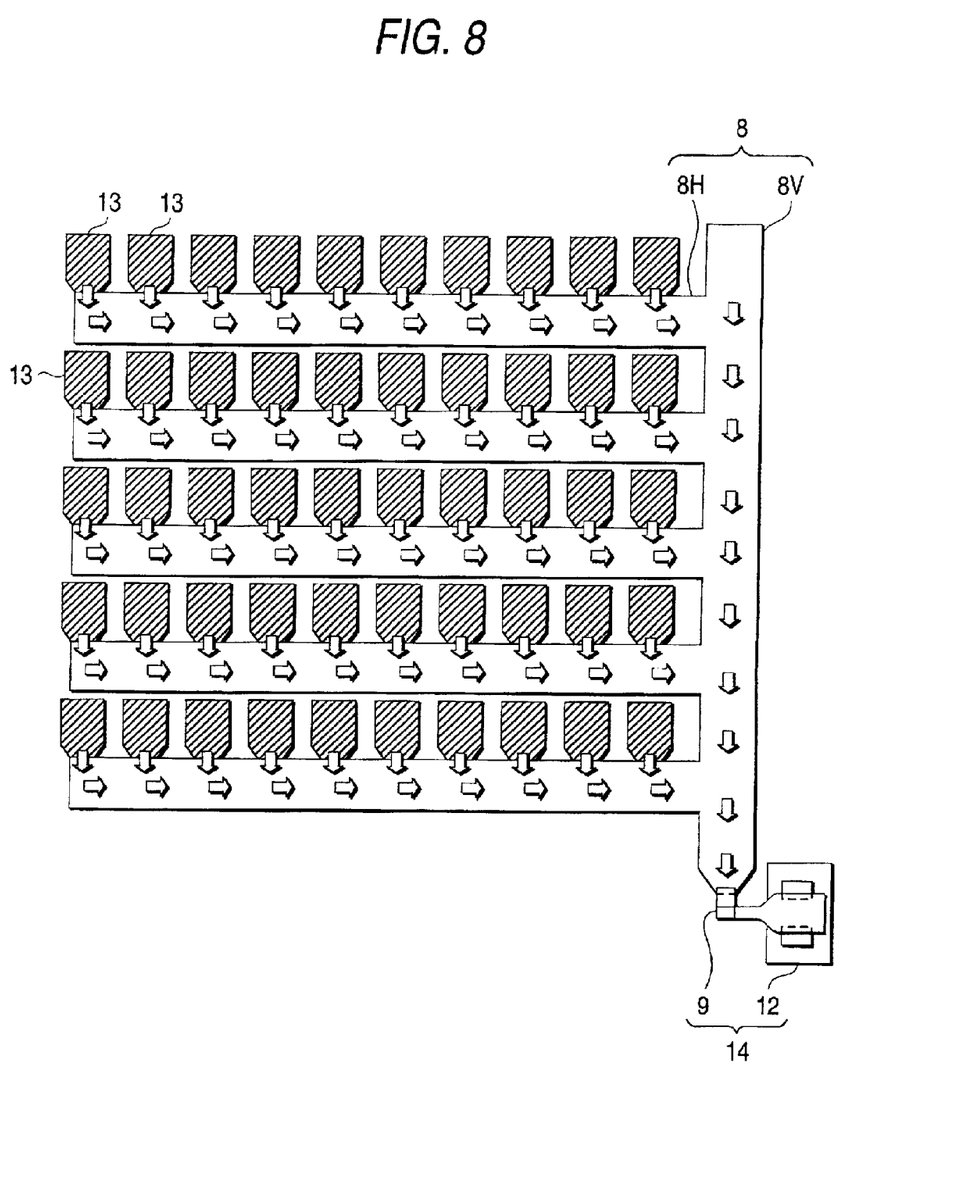
FIG. 8 is a view schematically showing the planar structure of a sensor section of the chemical CCD.

As shown in FIG. 8, the sensor sections 13 are arranged two-dimensionally to form an array. Thus, information on plural points can be fetched at the same time and signals on the points can be processed in order through the charge transfer section 8 and the output section 13. As shown in FIG. 8, the upper surface of the chemical CCD 1 includes a plurality of sensor sections 13 for converting a chemical phenomenon, for example, pH to electric charges, the charge transfer section 8 for transferring the electric charges obtained by the conversion in the sensor sections 13 in a direction of an arrow, and the output section 14 for converting the transferred electric charges into output signals, and the charge transfer section 8 includes a horizontal CCD 8H and a vertical CCD 8V.

The principle of measurement of the chemical CCD 1 will be described below with reference to a potential diagram of FIG. 9. For the measurement, a pulse voltage is applied to the charge supply section 4, the barrier section 7 and the reset gate 10, while a DC voltage is applied to electrodes other than the floating diffusion 9.

In an ordinary MOS structure using a p-type semiconductor, there has been known the fact that a depletion layer is formed on an interface between an insulating film and a semiconductor depending on a positive voltage to be applied to a metal electrode. By using this phenomenon, a potential state is set in the vicinity of the interface of the semiconductor and the insulating film as shown in FIG. 9.

Figure 9A:
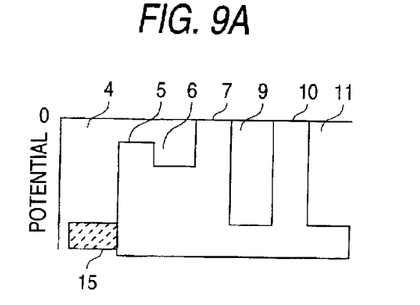
FIGS. 9A to 9F are views illustrating the principle of measurement of the CCD.

In a state 1, the electric potential of the charge supply section 4 is set to be high (in a direction of an arrow) and electric charges 15 are not injected into the sensing section 6 as shown in FIG. 9A.

Figure 9B:
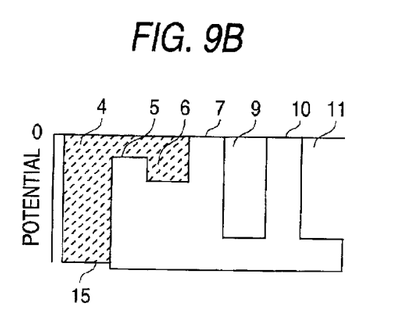

In a state 2, the electric charges 15 are injected into the sensing section 6 by reducing the electric potential of the charge supply section 4 as shown in FIG. 9B.

Figure 9C:
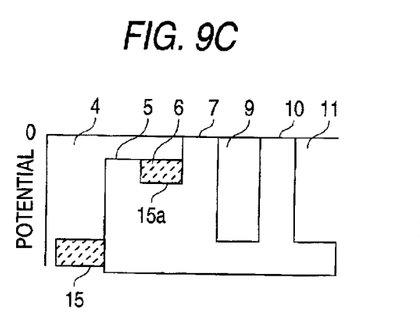

In a state 3, electric charges 15a taken out by the charge injection adjusting section 5 are accumulated in the sensing section 6 by increasing the electric potential of the charge supply section 4 as shown in FIG. 9C.

Figure 9D:
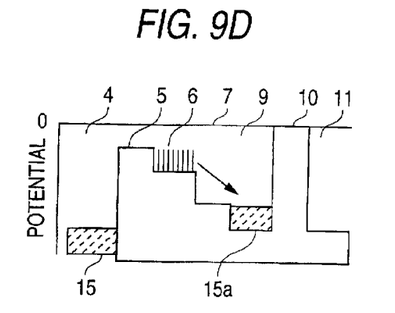

In a state 4, the electric charges 15a accumulated in the sensing section 6 are transferred to the floating diffusion 9 by increasing the electric potential of the barrier section 7 as shown in FIG. 9D.

Figure 9E:
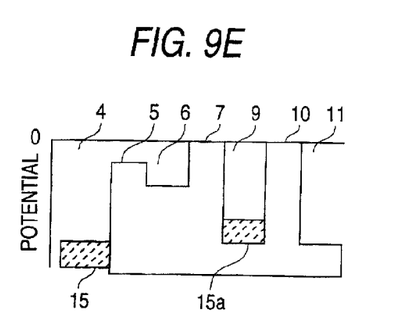

In a state 5, all the electric charges 15a of the sensing section 6 are transferred to the floating diffusion 9 to close the barrier section 7, thereby stopping the flow of the electric charges as shown in FIG. 9E. In this stage, the electric potential of the floating diffusion 9 is determined by the quantity of the electric charges 15a thus transferred. Therefore, the electric potential is input to a gate section of the output transistor 12 having the MOS structure, a drain current of the output transistor 12 is measured by a source follower circuit, for example, and the output is sent to a signal processor having a data processing function and an image processing function, for example, a computer (not shown).

Figure 9F:
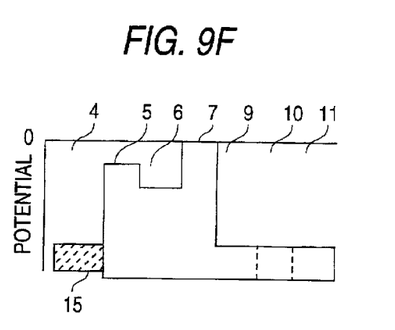

In a state 6, the electric potential of the floating diffusion 9 is read and the reset gate 10 is then turned on to reset to the electric potential of the reset drain 11 as shown in FIG. 9F. By the resetting, the same state as the state 1 is returned again. In other words, the electric charges can be output to the outside by repeating the operations of the states 1 to 6.

As is understood from the description with reference to FIG. 9, in the chemical CCD 1, the potential well (sensing section 6) constituted to change a depth corresponding to the chemical quantity is formed on the semiconductor substrate 2, the electric charges 15 are injected into the potential well 6 and the physical or chemical quantity is converted into electric charges corresponding to the size of the potential well. Thus, the scale of a chemical phenomenon is measured. According to the chemical CCD 1, the chemical phenomenon in a plurality of different positions can be measured at the same time. Since the chemical quantity is converted into the electric charges, the one-dimensional distribution or two-dimensional distribution of the chemical phenomenon can easily be formed into an image.

SUMMARY OF THE INVENTION

The invention has been made in consideration of the foregoing and has an object to provide a novel and useful molecular recognition type chemical CCD capable of measuring an ultramicro chemical substance with an ultrahigh sensitivity at a molecular level.

In order to achieve the object, the invention provides a molecular recognition type chemical CCD in which a molecular recognition layer is formed on a sensor face of a chemical CCD having such a structure that a plurality of potential wells constituted to change a depth corresponding to a chemical quantity are arranged two-dimensionally, electric charges are injected into the potential wells, and the chemical quantity is converted into an electric charge corresponding to the sizes of the potential wells.

For example, in the case in which the molecular recognition layer is formed by a molecule imprinting method, concentrations of various chemical substances including an environment pollutant such as dioxin or environmental hormone can be measured with a high sensitivity at a molecular level. If the molecular recognition layer can individually recognize various kinds of chemical substances, they can be detected at the same time.

According to the third aspect of the invention, moreover, the molecular recognition layer is constituted by a DNA complementary to a DNA to be measured. Thus, the DNA to be measured can be detected with a high sensitivity.

According to the fourth aspect of the invention, in the case in which a gel having a solution containing a substance to be measured mixed into a gel material for migration is provided on an upper surface of the molecular recognition layer and a DC voltage is applied to the gel to measure the substance to be measured in the gel which is obtained after electrophoresis, the substance to be measured can be measured in a separation state.

DETAILED DESCRIPTION OF THE PREFERRED EMBODIMENTS

An embodiment of the invention will be described with reference to the drawings. FIGS. 1 to 4 show a first embodiment of the invention. In a molecular recognition type chemical CCD 20 according to the embodiment, a molecular recognition layer 21 is formed on a sensor face 6a of the chemical CCD 1 described above as shown in FIG. 1. The molecular recognition layer 21 is formed by the molecule imprinting method described above, for example.

Figure 3:
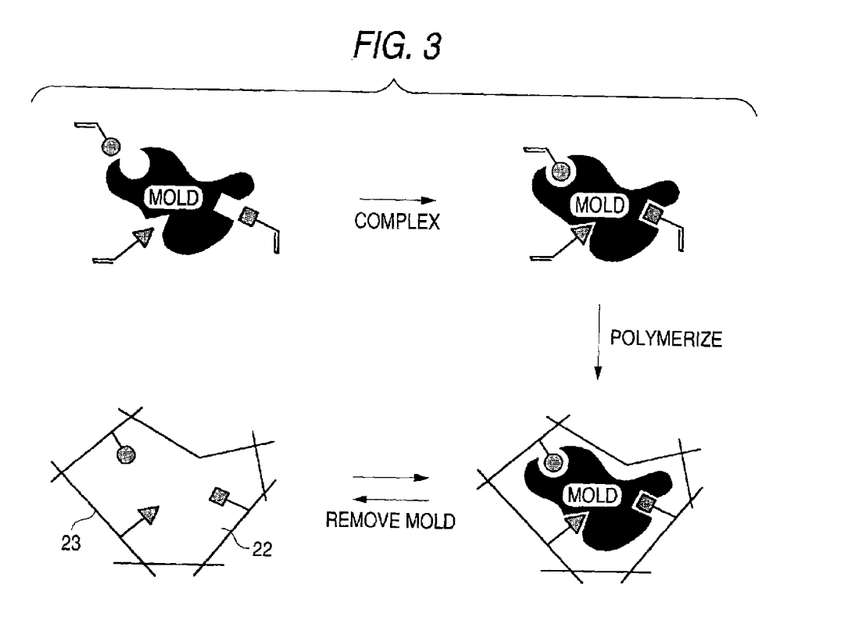
FIG. 3 is a view schematically illustrating a molecule imprinting method for forming the molecular recognition layer.

In the molecule imprinting method, as shown in FIG. 3, when a polymeric resin is a host and a substance to be measured, for example, dioxin is a guest, they are complexed and polymerized and the dioxin to be the guest is then removed by washout so that a mold 23 having a cavity 22 in a portion of the host where guest molecules are present is formed to take out only molecules corresponding to the mold 23. The molecular recognition layer 21 can simultaneously measure other chemical substances such as environmental hormone (chemical substances which work like hormone in human body) as well as the dioxin.

Figure 2A:
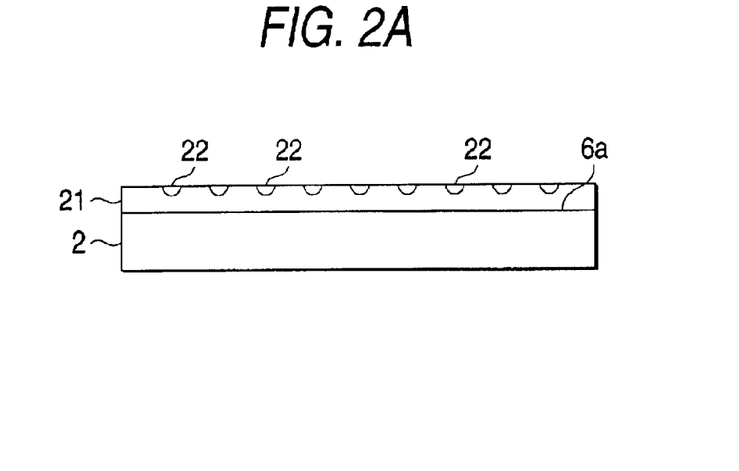
FIGS. 2A and 2B are a sectional view and a plan view typically showing an example of a molecular recognition layer in the molecular recognition type chemical CCD.
Figure 2B:
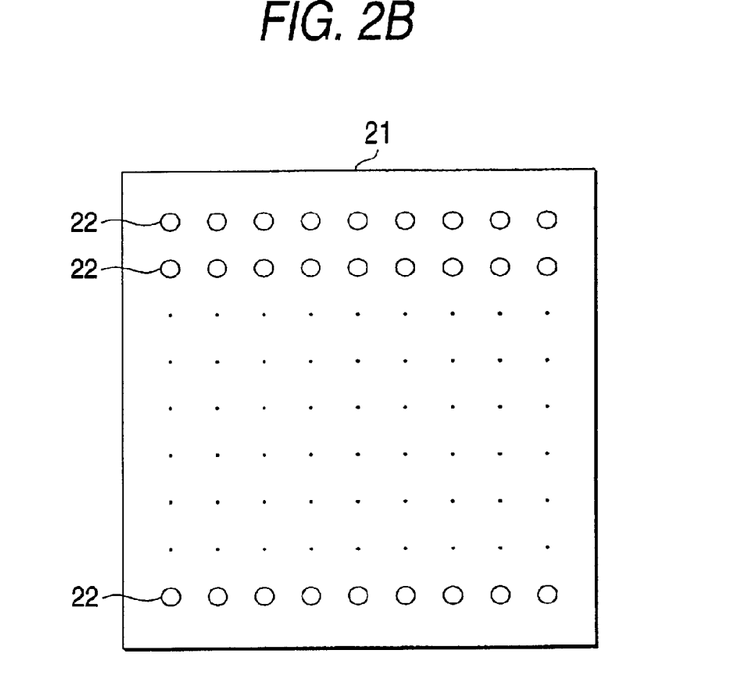

As is typically shown in FIG. 2, a plurality of molecular recognizing sections 22 having electrical cavities formed by the molecule imprinting method are arranged two-dimensionally on the molecular recognition layer 21 formed on the sensor face 6a of the chemical CCD 1. The molecular recognition layer 21 is fabricated in a silicon wafer process and comprises pyrrole to be a conductive polymer, for example.

Figure 4:
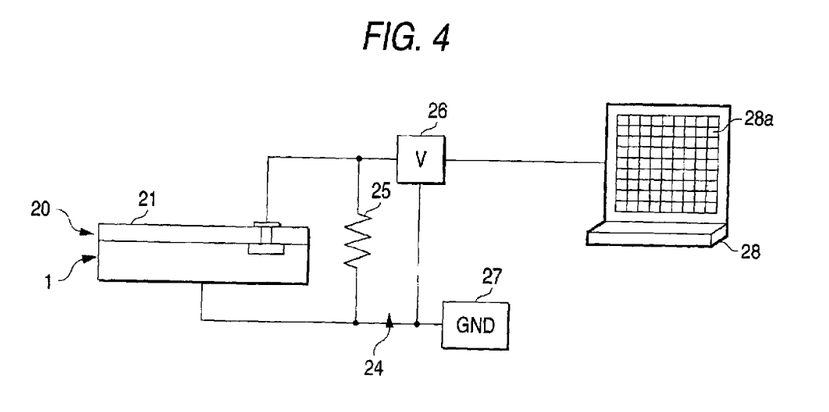
FIG. 4 is a diagram schematically showing the whole structure of the molecular recognition type chemical CCD.

FIG. 4 is a diagram showing an example of a structure in which a signal of the molecular recognition type chemical CCD 20 is processed and a result of measurement is displayed. In FIG. 4, the reference numeral 24 denotes a source follower circuit including a resistor 25, an output terminal 26 and a ground terminal 27. An output signal of the circuit 24 is greatly varied depending on a magnitude of the resistor 25 and can obtain a linear voltage signal for an output current. The reference numeral 28 denotes a computer having a data processing function and an image processing function which includes a display 28a capable of carrying out color display. Thus, the result of processings and the situation of distribution can be displayed properly.

Figure 1:
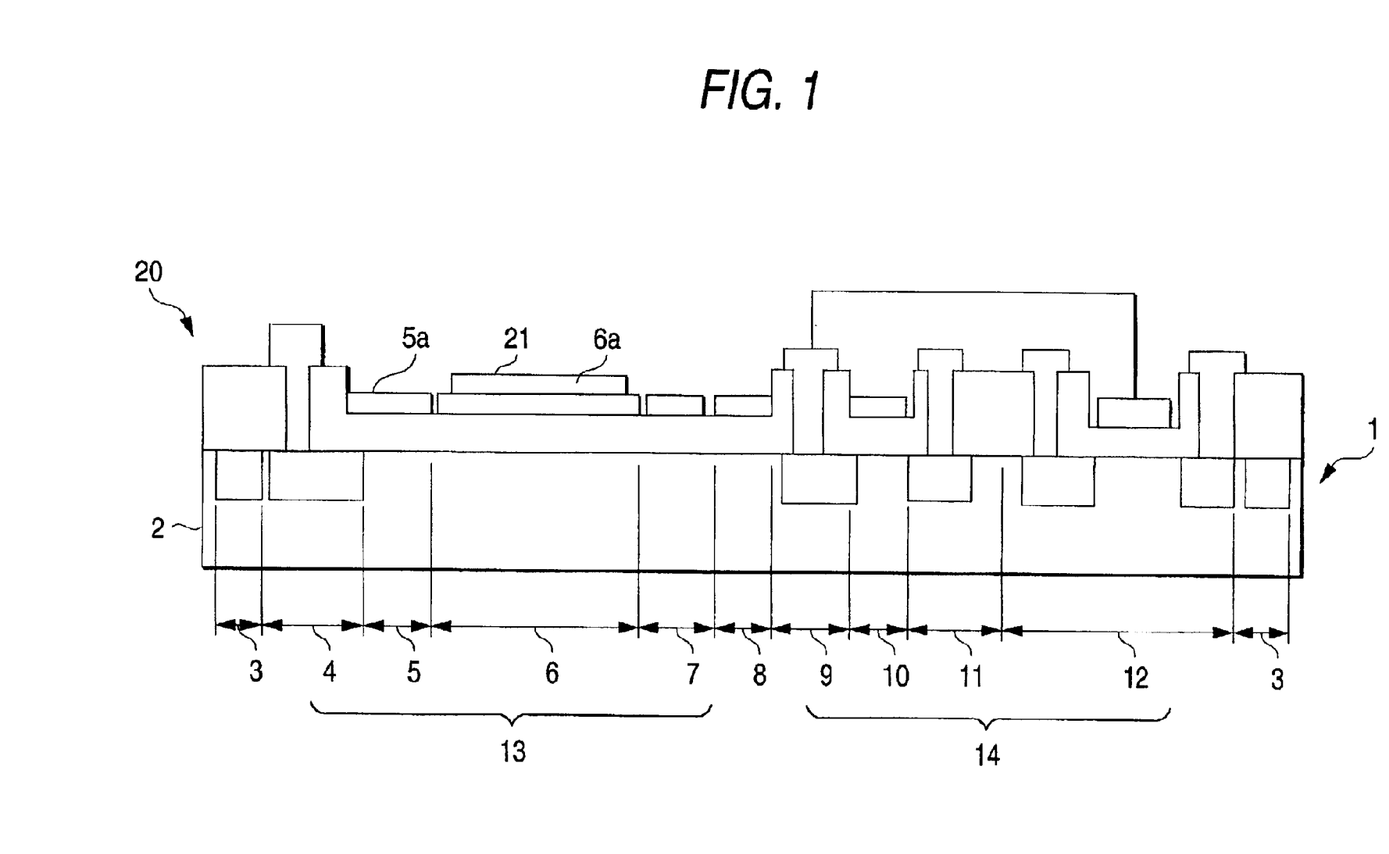
FIG. 1 is a view schematically showing the structure of a main part of a molecular recognition type chemical CCD according to the invention.

According to the molecular recognition type chemical CCD 20 having such a structure, for example, when a very small quantity [for example, 1 nL (nanoliter)] of solution is dropped as a sample over the molecular recognition layer 21, a molecule of a chemical substance contained in the solution is recognized by the molecular recognizing section 22 formed corresponding to the molecule, and electric charges corresponding to the concentration of the chemical substance are output from the molecular recognizing section 22 and are taken out through the chemical CCD 1. Accordingly, the environmental pollutant such as dioxin or environmental hormone in the solution is simultaneously measured at a ppb or ppt level.

As described above, the molecular recognition type chemical CCD 20 according to the invention conforms to a surface potential measuring method on an electrode. Therefore, all charged substances can be measured by properly forming the molecular recognition layer 21.

While all the molecular recognizing sections 22 in the molecular recognition layer 21 may detect different chemical substances from each other, they may detect only a single chemical substance to measure two-dimensional distribution thereof.

Protein including a DNA can be measured by using the molecular recognition type chemical CCD 20 according to the first embodiment. In particular, the DNA can easily be measured by using the molecular recognition type chemical CCD having the following structure. A second embodiment will be described below.

Figure 5A:
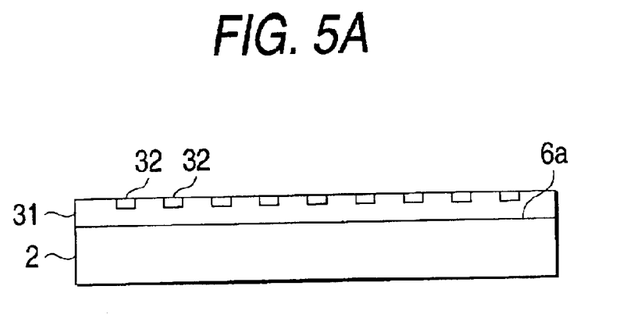
FIGS. 5A and 5B are a sectional view and a plan view typically showing another example of the molecular recognition layer.
Figure 5B:
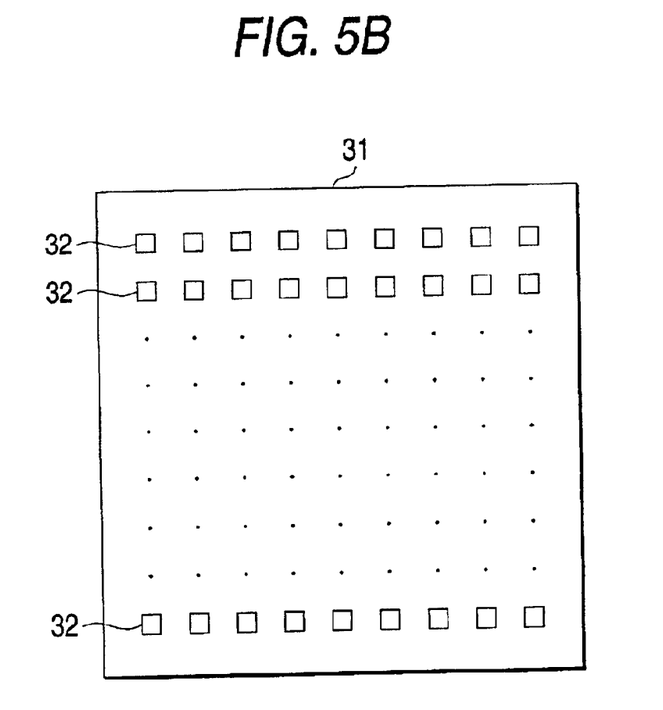

FIGS. 5A and 5B typically show the structure of a sensor section of a molecular recognition type chemical CCD 20A according to the second embodiment. In FIGS. 5A and 5B, the reference numeral 31 denotes a molecular recognition layer formed on a sensor face 6a of the chemical CCD 1, in which a DNA complementary to a DNA to be measured is arranged two-dimensionally. In FIGS. 5A and 5B, the reference numeral 32 denotes a complementary DNA.

In the molecular recognition type chemical CCD 20A having such a structure, it is possible to detect a DNA contained in a very small quantity of sample liquid which is put on the molecular recognition layer 31.

Figure 6A:
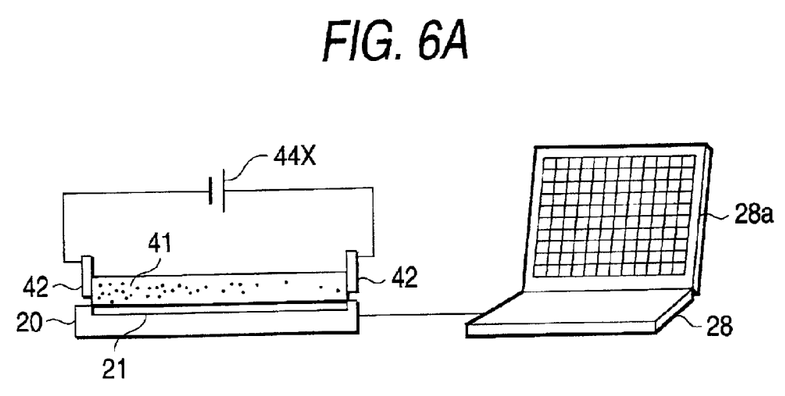
FIGS. 6A and 6B show another embodiment of the invention.
Figure 6B:
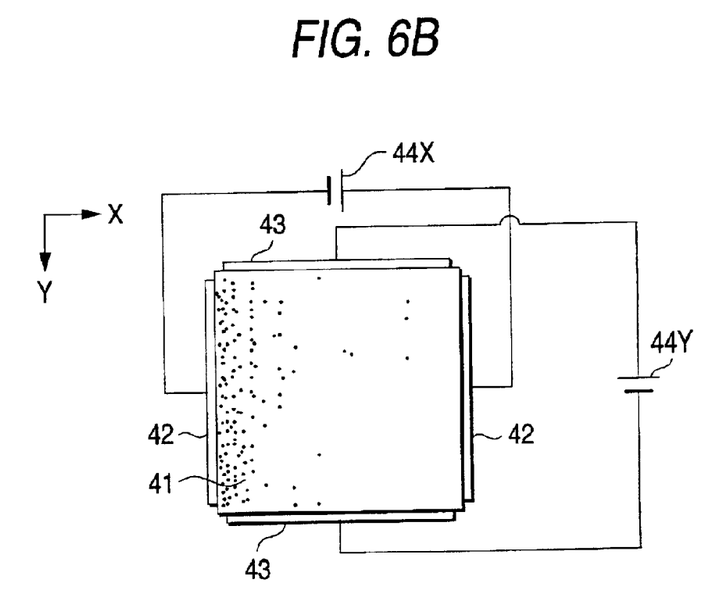

FIGS. 6A and 6B show a third embodiment of the invention. In the embodiment, as shown in FIG. 6A, a substance to be measured is mixed to a gel material for migration such as acrylamide or agar to form a sheet-shaped gel 41, for example, and the gel 41 is provided on a molecular recognition layer 21 of the molecular recognition type chemical CCD 20 shown in FIG. 1. As shown in FIG. 6B, a pair of electrodes 42 and 43 are provided in two orthogonal directions (X and Y directions) of the gel 41. A dc voltage is applied to the electrodes 42 and 43 to electrophorese the substance to be measured in the gel 41. In such a case, the substance to be measured can be measured in a separation state. The reference numerals 44X and 44Y denote DC power sources.

In the third embodiment, the molecular recognition layer may use the structure shown in FIGS. 5A and 5B.

According to the molecular recognition type chemical CCD of the invention, the ultramicro chemical substance can be measured with an ultrahigh sensitivity at a molecular level. If the molecular recognition layer can individually recognize different kinds of chemical substances, a plurality of different chemical substances can be detected at the same time.

What is claimed is:

1. A molecular recognition type chemical CCD comprising:
    a chemical CCD having a plurality of potential wells constituted to change a depth corresponding to a chemical quantity, and being arranged two-dimensionally, in which electric charges are injected into the potential wells and the chemical quantity is converted into an electric charge corresponding to the sizes of the potential wells;
    a molecular recognition layer formed on a sensor face of a chemical CCD,
    said molecular recognition layer being structured to selectively capture molecular of certain chemical substances to allow the chemical CCD to output signals corresponding to the captured molecules.

2. The molecular recognition type chemical CCD according to claim 1, wherein the molecular recognition layer is formed by a molecule imprinting method in which a host polymeric resin and a guest substance to be measured are complexed and polymerized, and said guest substance is then removed to form a mold having a cavity in a portion of the host polymeric resin where the guest substance was present.

3. The molecular recognition type chemical CCD according to claim 1, wherein the molecular recognition layer comprises a DNA complementary to a DNA to be measured.

4. The molecular recognition type chemical CCD according to any of claims 1 to 3, wherein a gel having a solution containing a substance to be measured mixed into a gel material for migration is provided on an upper surface of the molecular recognition layer and a DC voltage is applied to the gel to measure the substance to be measured in the gel which is obtained after electrophoresis.

* * * * *